United States Patent [19]

Wald et al.

[11] 4,059,646

[45] Nov. 22, 1977

[54] PROCESS FOR PRODUCING TRIPTANE BY CONTACTING METHANOL OR DIMETHYL ETHER WITH ZINC BROMIDE

[75] Inventors: Milton M. Wald; Leo Kim, both of Houston, Tex.

[73] Assignee: Shell Oil Company, Houston, Tex.

[21] Appl. No.: 619,117

[22] Filed: Oct. 2, 1975

[51] Int. Cl.$^2$ .......................... C07C 1/20; C07C 9/16
[52] U.S. Cl. ................................ 260/676 R; 252/441; 260/666 R; 260/683.4 R; 260/683.43; 260/683.47; 260/683.64; 44/80
[58] Field of Search ........ 260/666 R, 676 R, 683.4 R, 260/683.43, 683.47, 683.64

[56] References Cited

U.S. PATENT DOCUMENTS

| | | | |
|---|---|---|---|
| 2,456,584 | 12/1948 | Gorin et al. | 260/676 R X |
| 2,492,984 | 1/1950 | Grosse et al. | 260/676 R |

*Primary Examiner*—Floyd D. Higel
*Attorney, Agent, or Firm*—Albert J. Adamcik

[57] ABSTRACT

Method for the production of triptane comprising contacting a reactant selected from methanol, dimethyl ether, or mixtures thereof, with zinc bromide at a temperature of from about 210° to about 245° C.

7 Claims, No Drawings

PROCESS FOR PRODUCING TRIPTANE BY CONTACTING METHANOL OR DIMETHYL ETHER WITH ZINC BROMIDE

BACKGROUND OF THE INVENTION

This invention relates to the production of organic compounds, especially hydrocarbons, from starting materials such as methanol, dimethyl ether, and mixtures thereof. More particularly, the invention provides a novel process for the production of branched chain hydrocarbons, particularly triptane, from methanol, dimethyl ether, or mixtures thereof.

Prior experimental work with methanol conversion to hydrocarbons may be characterized as largely academic or substantially un-economic in present terms. For example, as early as 1878, LeBel and Greene (Compt. rend., vol. 87, p. 260) produced alkyl hydrocarbons by contacting methanol with zinc chloride at elevated temperatures. More recently, Grosse and Snyder describe and claim a process in U.S. Pat. No. 2,492,984 wherein a mixture consisting essentially of a specified metal halide and at least one compound selected from the group consisting of methanol and dimethyl ether is subjected to conversion conditions, including a temperature of 250° to 650° C, to form substantial amounts of recoverable hydrocarbons having at least four hydrocarbons. The examples of the patent employ a zinc chloride catalyst, and the specification mentions that higher atomic weight halides of metals such as zinc, cadmium, thorium, and the like, may be used.

However, results reported in the patent are far from satisfactory, insofar as disclosure of suitable yields of high grade gasoline components is concerned. Conversions of up to 50 percent of recoverable hydrocarbons of four carbon atoms, based on the mols of methanol or dimethyl ether converted, are claimed. However, the experiments disclosed report, at best, a fraction containing about 20 percent (on the same basis) of recoverable hydrocarbon material boiling between 25° C at atmospheric pressure and 85° C at 1.5 mm. of Hg pressure (about 246° C at atmospheric pressure). No mention is made of the production of triptane (2, 2, 3-trimethyl butane), a heptane and a valuable fuel component.

The high cost of petroleum-based fuels and the potential availability of large quantities of methanol, e.g., methanol derived from synthesis gas or methane, have given rise to efforts to convert this methanol into higher grade fuels. Because of the superiority of triptane as a blending agent for high-grade gasoline, a process for producing triptane, as well as other hydrocarbons, from methanol or dimethyl ether could have great economic importance.

SUMMARY OF THE INVENTION

Accordingly, the invention provides a process for the production of triptane, comprising, contacting a material such as methanol, dimethyl ether, or mixtures thereof, with an effective amount of zinc bromide at a temperature of from about 210° to about 245° C. In its preferred form, the invention comprises a process for the production of triptane wherein methanol is contacted with an effective amount of zinc bromide at a temperature of from about 215° to about 240° C.

The source of the methanol employed is a matter of choice. For example, methanol derived from snythesis gas produced from coal, and methanol produced from natural gas are eminently suited to the practice of the invention. The purity of the methanol is not critical, provided the impurities do not interfere with the reaction. Thus, small amounts of water and ethanol, common impurities in methanol, do not interfere. Similarly, the presence of small amounts of synthesis gas from a synthesis gas conversion system does not interfere substantially with the methanol conversion reaction. The degree of purity of the methanol employed will, of course, affect the quantity of triptane produced, when considered with respect to total volume of feed material to the reactor, but the decision to use greater purity methanol must be viewed in the light of the increased cost of purification of the methanol prior to use. In general, dilute streams of methanol may be used, provided, as noted, the diluents do not interfere with the activity of the zinc bromide. The term "methanol" as used in the specification and claims, is intended to include the use of such dilute streams containing methyl alcohol. Moreover, any material which will react to provide methanol in situ under the reaction conditions specified herein, and which does not interfere with the reaction, and whose other reaction product or products, if any, do not interfere with the conversion reaction, is within the scope of the invention. For example, since dimethyl ether decomposes under the reaction conditions employed to form methanol, dimethyl ether may be used as a source of methanol, either as the total feed, or a portion thereof. Under some conditions, disclosed herein, significant quantities of dimethyl ether may be formed. This dimethyl ether may be separated and recycled, thereby providing a highly efficient use of source materials.

In the same manner, the zinc bromide employed need not be pure, but may contain impurities which do not interfere with the reaction. Commercial grade zinc bromide is acceptable in the process of the invention, and the low cost of zinc bromide and its ease of recovery are advantages of the invention.

The temperatures employed in the reaction are significant. Although triptane is produced in the presence of zinc bromide at temperatures above 250° C, greater selectivity of the reaction to triptane is obtained at temperatures of from about 210° to 245° C. As indicated, the preferred temperature range is from about 215° to about 240° C, with temperatures of from about 220° to about 235° C being most preferred. Selectivities to triptane are superior, at the general temperatures indicated, and much superior at the preferred temperatures, to those obtained at 250° C or above, even though total quantities of reaction product may be roughly the same or even less.

Pressures employed in the reaction zone are not critical, and may vary widely. Thus, pressures may be atmospheric, below atmospheric, or greater than atmospheric. As a practical matter, pressure in a batch-type system may be atmospheric initially, but will rise as temperatures are raised. Pressures on the order of 2000 p.s.i.g. or even higher may be used, and the selection of the appropriate pressure to be employed is well within the skill of the art.

The ratio of methanol to $ZnBr_2$ is significant, and an effective amount, i.e., an amount sufficient to initiate and sustain the reaction must be employed. Those skilled in the art may readily determine appropriate amounts, keeping in mind that excessively high ratios of methanol to $ZnBr_2$ may not be used. For example, ratios of from about 0.01 mol of methanol per mol of $ZnBr_2$ to about 24 mols of methanol per mol of $ZnBr_2$ may be used, while ratios of from about 0.1 mol of methanol per mol of $ZnBr_2$ to about 10 mols of methanol per mol of $ZnBr_2$ are preferred. In the case of dimethyl ether as a feed, the ratio of feed to $ZnBr_2$ would be similar, and where dimethyl ether is used as a portion of the feed, adjustment of the ratios may be made accordingly.

The process may be conducted batch-wise or in a continuous fashion. Whichever procedure is employed, good mixing or contact of the $ZnBr_2$ and methanol is important for good results. Any reaction system which provides a high degree of mixing or contact of the methanol and $ZnBr_2$ may be employed. For example, fixed bed systems, slurry reactors, and trickle bed reactors may be used. Contact times are not critical, and those skilled in the art may vary the contact times to provide sufficient contact time to produce optimum results, depending on, e.g., volume of reactants, reactor design, temperature, etc. For example, utilizing a fixed bed reactor design, and continuous flow of reactants, contact times on the order of from about 0.5 minute (245° C) to about 120 minutes, or 180 minutes, (225° C), or even longer may be used. Where batch procedures are employed, contact times may be considerably longer. In both batch and continuous procedures, it is not necessary that 100 percent conversion of the methanol be obtained before recovering the product, the methanol being easily separable and recyclable. The triptane may be separated from the other reaction products before use, or the reaction products mixture may be used directly as a fuel or blending agent.

DETAILED DESCRIPTION OF THE INVENTION

In order to describe the invention with greater particularity, reference is made to the following example:

About 200 grams of $ZnBr_2$ and 40.0 grams (50 ml.) of methanol were combined under nitrogen in an autoclave and the autoclave was then sealed. The pressure was raised to 200 p.s.i.g. with nitrogen, and the mixture was stirred and heated to about 225° C for 1 hour. The reactor was then cooled to room temperature and the pressure reduced to about 210 p.s.i.g. Gaseous product and nitrogen were vented into a water displacement gas holder. Liquid product was distilled from the reactor at about 100° C to a cold trap, first at atmospheric pressure with slow nitrogen flow (30 min.), and then at reduced pressure (30 min. at 20 mmHg, then 15 min. at 2 mmHg). The material remaining in the autoclave (mainly $ZnBr_2$) was washed out with water.

Gaseous product was small in amount, and consisted mainly of isobutane with some higher isoparaffins. Very little methane, ethane, or propane were found. The liquid product in the cold trap comprised two layers, a lower aqueous layer and an upper hydrocarbon phase. The lower layer was essentially water, very little methanol being present. The hydrocarbon layer (5.04 grams) gave the following analysis:

| Compounds | Percent by weight |
| --- | --- |
| isopentane | 11.2 |
| isohexanes | 13.5 |
| triptane | 47.4 |
| other heptanes and isooctanes | 10.8 |
| $C_9$ to $C_{13}$ hydrocarbons | 15.3 |
| $CH_3 Br$ | Trace |
| $CH_3O CH_3$ | Trace |

What we claim is:

1. A method for the production of triptane comprising contacting a material selected from the group consisting of methanol; dimethyl ether; other materials which react to provide methanol in situ, other reaction products, if any, being non-interfering; and mixtures thereof, with an effective amount of $ZnBr_2$ at a temperature of from 210° to 245° C.

2. The method of claim 1 wherein the temperature is from 215° to 240° C.

3. The method of claim 1 wherein the temperature is from 220° to 235° C.

4. A method for the production of triptane comprising contacting methanol with an effective amount of $ZnBr_2$ at a temperature of from 210° to 245° C.

5. The method of claim 4 wherein the temperature is from 215° to 240° C.

6. The method of claim 4 wherein the temperature is from 220° to 235° C.

7. A method for the production of triptane comprising contacting dimethyl ether with an effective amount of $ZnBr_2$ at a temperature of from 210° to 245° C.

* * * * *